United States Patent [19]
Hopper et al.

[11] Patent Number: 5,697,946
[45] Date of Patent: Dec. 16, 1997

[54] METHOD AND APPARATUS FOR ANCHORING LAPAROSCOPIC INSTRUMENTS

[75] Inventors: Phillip K. Hopper, San Carlos; Tim J. Kovac, Los Gatos; Edmund J. Roschak, Belmont; Wilson Eng, San Jose, all of Calif.

[73] Assignee: Origin MedSystems, Inc., Menlo Park, Calif.

[21] Appl. No.: 320,042

[22] Filed: Oct. 7, 1994

[51] Int. Cl.$^6$ ............................................. A61B 17/34
[52] U.S. Cl. ............................................................. 606/185
[58] Field of Search ............................... 606/1, 167, 185, 606/190–198; 604/164, 171, 174, 264, 96–104; 600/201, 204, 207; 128/898

[56] References Cited

U.S. PATENT DOCUMENTS

| | | | |
|---|---|---|---|
| 2,912,981 | 11/1959 | Keough | 128/349 |
| 3,039,468 | 6/1962 | Price | 606/185 |
| 3,050,066 | 8/1962 | Koehn | 128/349 |
| 3,253,594 | 5/1966 | Matthews et al. | 128/348 |
| 3,459,175 | 8/1969 | Miller | 128/2 |
| 3,528,869 | 9/1970 | Dereniuk | 156/294 |
| 3,543,759 | 12/1970 | McWhorter | 128/349 |
| 3,817,251 | 6/1974 | Hasson | 128/348 |
| 3,896,816 | 7/1975 | Mattler | 128/349 |
| 3,961,632 | 6/1976 | Moossun | 128/347 |
| 4,003,382 | 1/1977 | Dyke | 128/349 |
| 4,018,231 | 4/1977 | Wallace | 128/351 |
| 4,077,412 | 3/1978 | Moossun | 128/347 |
| 4,091,816 | 5/1978 | Elam | 128/351 |
| 5,002,557 | 3/1991 | Hasson | 606/191 |
| 5,122,122 | 6/1992 | Allgood | 604/174 |
| 5,147,316 | 9/1992 | Castillenti | 604/174 |
| 5,176,697 | 1/1993 | Hasson et al. | 606/191 |
| 5,201,742 | 4/1993 | Hasson | 606/130 |
| 5,217,441 | 6/1993 | Shichman | 604/283 |
| 5,290,249 | 3/1994 | Foster et al. | 604/174 |
| 5,330,497 | 7/1994 | Freitas et al. | 606/185 |
| 5,331,975 | 7/1994 | Bonutti | 606/192 |
| 5,345,927 | 9/1994 | Bonutti | 600/207 |
| 5,445,615 | 8/1995 | Yoon | 604/96 |

FOREIGN PATENT DOCUMENTS

| | | | |
|---|---|---|---|
| 0 526 721 A1 | 6/1992 | European Pat. Off. | A61B 1/32 |
| 0 589 452 A1 | 9/1993 | European Pat. Off. | A61B 17/34 |
| WO 93/09722 | 5/1993 | WIPO | A61B 17/02 |

*Primary Examiner*—Glenn Dawson
*Attorney, Agent, or Firm*—Limbach & Limbach L.L.P.

[57] ABSTRACT

A balloon anchor provides for the anchoring of a surgical instrument, such as conventional trocar sheath, within a puncture opening formed by a trocar. When used on a trocar sheath, the anchor is secured to the smooth outer surface of the sheath for extension through the puncture opening as the trocar within the sheath forms the opening. Adhesive or mechanical means are provided to secure the balloon the instrument. No modification to the structure of the instrument is required. Once in place within the opening, the balloon is inflated to the interior of the tissue to anchor the instrument in place. Certain embodiments also provide for inflation of the balloon within and/or to the exterior of the opening.

17 Claims, 11 Drawing Sheets

5,697,946

METHOD AND APPARATUS FOR ANCHORING LAPAROSCOPIC INSTRUMENTS

BACKGROUND OF THE INVENTION

The present invention relates to an improved anchor for securing laparoscopic instruments within puncture openings during surgery. In its more specific aspects, the invention is concerned with a balloon anchor adapted to be secured to the outside surface of virtually any laparoscopic instrument, without the necessity of modifying the structure of the instrument.

Laparoscopic surgery provides a minimally invasive approach to a wide variety of surgical procedures in, for example, the abdominal and thoracic cavities. In a minimally invasive approach, small incisions are made to provide access for instruments needed to perform surgery. The instruments, such as trocars, endoscopes, clip appliers, cautery devices and other tools, are commonly inserted through these small incisions using cannulas which are adapted to provide a pressure seal when using pneumoperitoneum. It is desirable to secure or anchor these cannulas into position in the incision to allow easy insertion and withdrawal of instruments through the cannula without corresponding movement of the cannula. Likewise, it is sometimes desirable to secure or anchor an instrument itself in an incision and prevent unwanted distal or proximal movement of the instrument.

Prior anchors for laparoscopic instruments have employed threaded sleeves adapted to be secured to the instruments and screwed into a laparoscopic puncture opening to secure the instrument in place. An anchor of this type is found in U.S. Pat. No. 5,217,441. Such anchors require a specific size for each size of instrument, since the sleeve must be of a configuration complemental to that of the instrument. The screw threads also must be twisted into place and are relatively traumatic.

The prior art also teaches adhesive anchors, sometimes called "grippers," for securing laparoscopic instruments in place within puncture openings. Such anchors employ a tubular boss configured to snugly engage the instrument and a flexible disk carried by the boss for adhesion to the outside surface of the punctured tissue. The boss must be specifically configured to match the configuration of the instrument being anchored. Blood emitting from the puncture opening often intrudes between the disk and the tissue so as to destroy the integrity of the anchor during surgery.

The prior art also teaches the provision of specially constructed laparoscopic cannula provided with inflatable balloons to anchor the cannula in place within a puncture opening. A cannula of this type may be seen in U.S. Pat. No. 5,002,557. Such cannula are expensive to fabricate and must be especially configured to match the instrument with which they are used.

It is also old in the art to anchor drainage catheters with balloons incorporated into the catheter. One well-known catheter of this type used for urinary drainage is the "Foley" catheter. In such catheters, the balloon and the conduit provided for its inflation is integrally molded into the catheter.

SUMMARY OF THE INVENTION

The present invention is an improvement over the prior art in that it provides a universal balloon anchor which may be secured to the outside of a laparoscopic instrument and inflated to anchor the instrument in place within a puncture opening. The balloon is configured so as to have a low profile generally contiguous with the outside surface of the instrument to facilitate its low insertion force placement and removal, without significant trauma to the tissue defining a small laparoscopic opening.

In its broadest aspects, the anchoring system of the invention provides a low profile balloon adapted to be engaged with the outside surface of a laparoscopic instrument. In the preferred embodiments, the balloon is adhesively secured to the instrument. Certain embodiments also employ mechanical structure to constrain the balloon and hold it in place. Conduit means for inflating the balloon is also secured externally of the instrument being anchored.

In the method of the invention, the balloon is secured to the outer surface of an instrument to be anchored with the balloon in a deflated low profile configuration essentially contiguous with the outer surface of the instrument. The instrument is then extended through the puncture opening within which it is to be anchored so as to dispose at least a portion of the balloon to the inside of the opening. The balloon is then inflated to anchor the instrument.

A principal object of the invention is to provide a universal anchor which may be secured to virtually any instrument used for laparoscopic surgery to anchor the instrument within a puncture opening.

Another and related object is to provide such an anchor which is inexpensive and may be used with a minimum of trauma to the punctured tissue.

Yet another object of the invention is to provide such an anchor which can accommodate puncture openings formed in tissues of different wall thicknesses.

Still another object of the invention is to provide such an anchor which may form a seal around the puncture.

Still another and more specific object of the invention is to provide such an anchor which may lock the instrument against movement either into or out of a puncture opening.

A further object of the invention is to provide such an anchor which may be used for both gasless- and gas- (insufflation) type laparoscopic surgery.

Another object of the invention is to provide such an anchor which may be located anywhere along the length of a laparoscopic instrument and which can be used in multiples, if desired.

Yet a further object of the invention is to provide such an anchor which is ideally suited for one-time use and does not have such bulk as to create undue disposal problems.

The foregoing and other objects will become more apparent when viewed in light of the following detailed description and accompanying drawings.

DESCRIPTION OF THE PREFERRED EMBODIMENTS

FIRST EMBODIMENT

Figure 1:
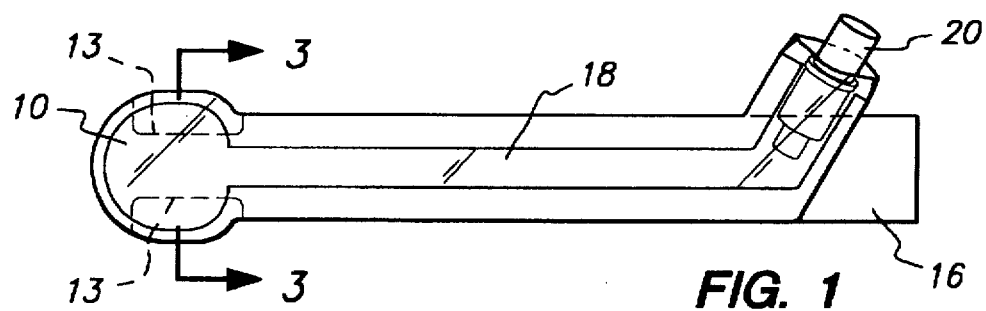
FIG. 1 is a plan of a first embodiment of the anchor, employing a balloon provided with an adhesive backing wherein a shielding strip is temporarily disposed over the backing.
Figure 2:
FIG. 2 is an elevational view of the anchor shown in FIG. 1.
Figure 3:
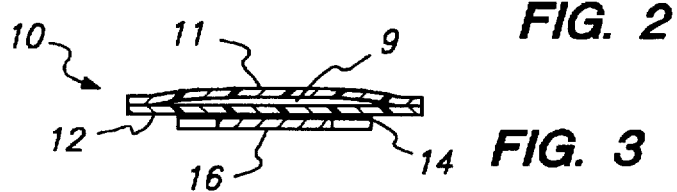
FIG. 3 is a cross-sectional view of the anchor shown in FIG. 1, taken on the plane designated by line 3—3.

As shown in FIGS. 1–3, this embodiment comprises an elastomeric balloon 10 having a first film layer 11 of elastic or semi-elastic material, and a second film layer 12 of elastic, semi-elastic or inelastic material. Second film layer 12 is ideally very flexible so that it can easily confirm to the outside surface of an instrument such as a trocar sheath. Preferably, first film layer 11 and second film layer 12 are made of material suitable for medical applications having a good strength to thickness ratio. Thinner materials facilitate lower deflated profiles and thus lower incision insertion forces. First film layer 11 can be made of urethane or other appropriate film. A semi-elastic PS-8010 polyurethane film, referred to as PS-8010, manufactured by Deerfield Urethane of Deerfield, Mass. is suitable. Second film layer 12 is preferably a flexible inelastic material, such as polyester. A suitable material is Rexham 705517 manufactured by Rexham Industrial, Inc. of Matthews, N.C. Alternatively, first and second film layers 11, 12 can be made of the same elastic or semi-elastic material if desired. A contact adhesive 14 is adhered to the undersurface of second layer 12 and covered by a removable paper or plastic shielding strip 16. Contact adhesive 14 and corresponding shielding strip 16 are cut-away at portions 13 to facilitate unrestrained expansion of the balloon upon inflation. An inflation tube 18 is integrally formed by bonding first and second film layers 11, 12 together. A check valve or stop cock 20 is secured to the proximal end of the tube 18 for purposes of introducing inflation fluid (liquid or gas) into the tube 18.

In the embodiment illustrated, the balloon 10 is formed by peripherally bonding first layer 11 and second layer 12 together thereby creating a sealed inflatable chamber 9 therebetween. An alternative construction for the balloon would be to fabricate the balloon as a closed elastomeric envelope with contact adhesive applied directly one side of the envelope. With such a construction, a removable paper or plastic shielding strip would also be provided over the adhesive. In use, the balloon of such a construction would be adhered directly to an instrument with the contact adhesive. The surface of the instrument would serve as the inelastic backing restraining the balloon from elongation upon inflation.

Figure 4:
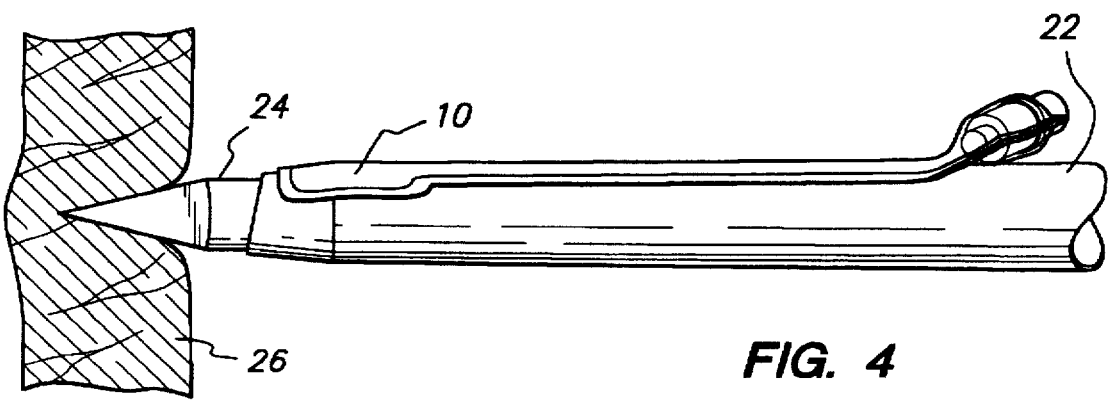
FIG. 4 is an elevational view of the FIG. 1 anchor in place on a trocar sheath, with the balloon of the anchor in a deflated condition and a trocar extended through the sheath in the process of forming a puncture opening in a tissue layer.

FIG. 4 illustrates the first embodiment balloon attached to the smooth outer surface of an instrument, in this case a conventional trocar sheath 22. As there shown, the shielding strip 16 has been removed from the adhesive 14 and the second film layer 12 is adhered to the sheath by the adhesive. In the deflated condition shown in FIG. 4, the balloon 10 and tube 18 have a low profile essentially contiguous with the outside surface of the sheath 22.

FIG. 4 also shows a sharp tipped trocar 24 extending through the sheath 22 and into piercing engagement with a layer of living tissue 26 such as an abdominal wall. The sheath 22 is telescopically received on the trocar 24 and moves with the trocar through the tissue 26.

Figure 5:
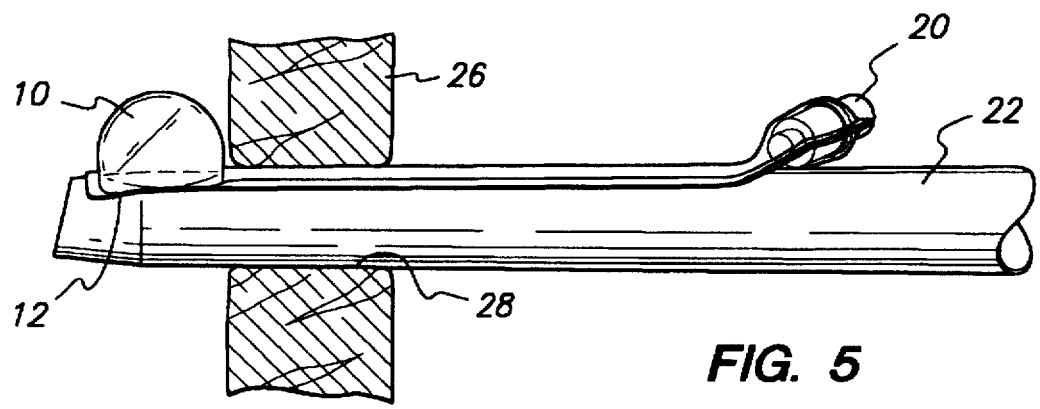
FIG. 5 is an elevational view similar to that of FIG. 4, showing the sheath fully extended through the puncture opening, with the balloon inflated and the trocar removed from the sheath.
Figure 6:
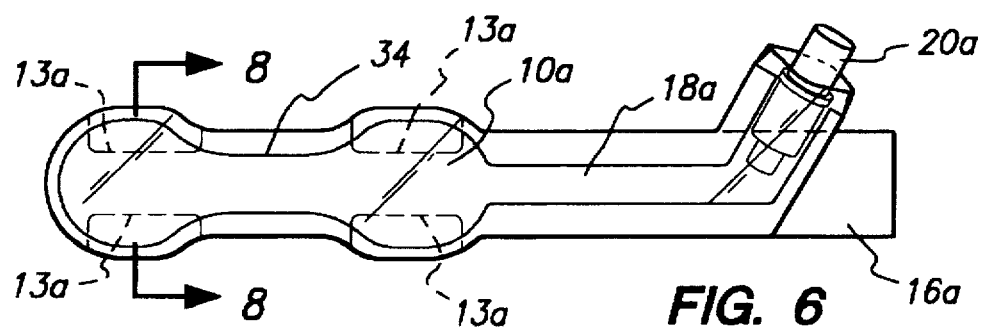
FIG. 6 is a plan view of a second embodiment of the anchor, employing a balloon of an elongate generally hourglass-shaped configuration provided with an adhesive backing wherein a shielding strip is temporarily disposed over the backing.
Figure 7:
FIG. 7 is an elevational view of the anchor shown in FIG. 6.
Figure 8:
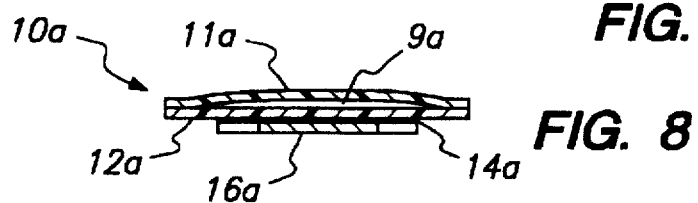
FIG. 8 is an cross-sectional view of the anchor shown in FIG. 6, taken on the plane designated by line 8—8.

FIG. 5 shows the sheath 22 extended fully through a puncture opening 28 which has been formed by the trocar 24, with the trocar removed from the sheath. As shown in FIG. 5, the balloon 12 has been inflated to the interior of the tissue to anchor the sheath distally against removal from the puncture. With the sheath so anchored, other instruments can be passed therethrough for diagnostic or surgical purposes and withdrawn from the sheath without unwanted proximal movement of the sheath. Upon completion of the procedure, the balloon 12 is deflated to return to the condition shown in FIG. 4 and the sheath may be removed from the incision with a minimum of trauma.

SECOND EMBODIMENT

This embodiment is illustrated in FIGS. 6–10 and is similar to the first embodiment, with the exception that the balloon 10a is of an elongate hourglass-shaped configuration. Parts of the second embodiment corresponding to those of the first embodiment are designated by like numerals followed by the letter a, as follows: elastic balloon 10a; first layer 11a; second layer 12a; chamber 9a; adhesive cut-away portions 13a; contact adhesive 14a; shielding strip 16a; inflation tube 18a; and check valve or stop cock 20a.

Figure 9:
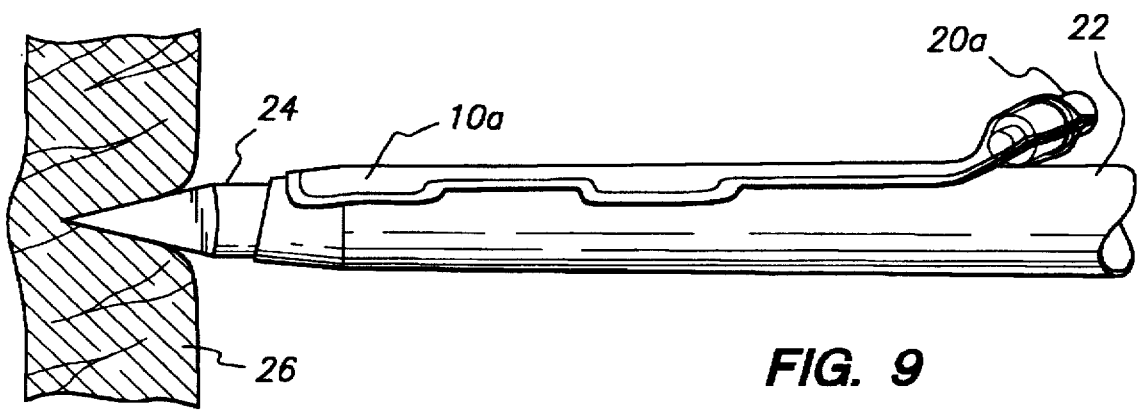
FIG. 9 is an elevational view of the FIG. 6 anchor in place on a trocar sheath with the balloon of the anchor in a deflated condition and a trocar extended through the sheath in the process of forming a puncture opening in a tissue layer.
Figure 10:
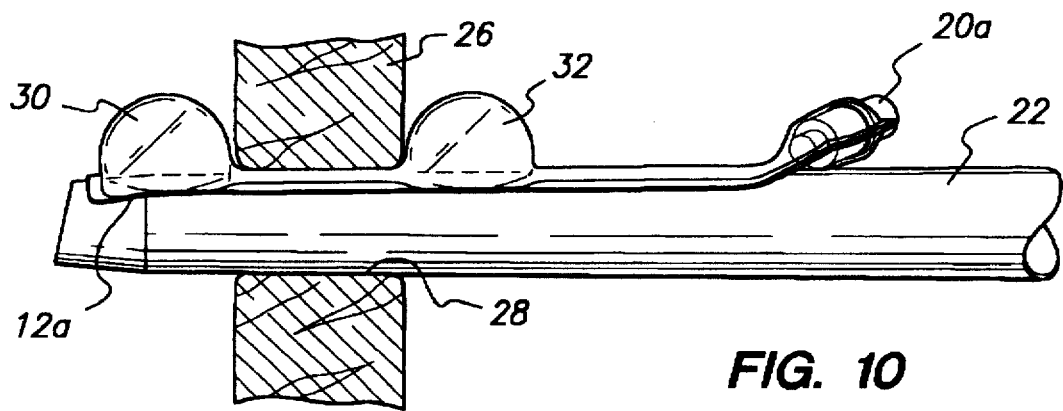
FIG. 10 is an elevational view similar to FIG. 9, showing the sheath fully extended through the puncture opening, with the balloon inflated and the trocar removed from the sheath.
Figure 11:
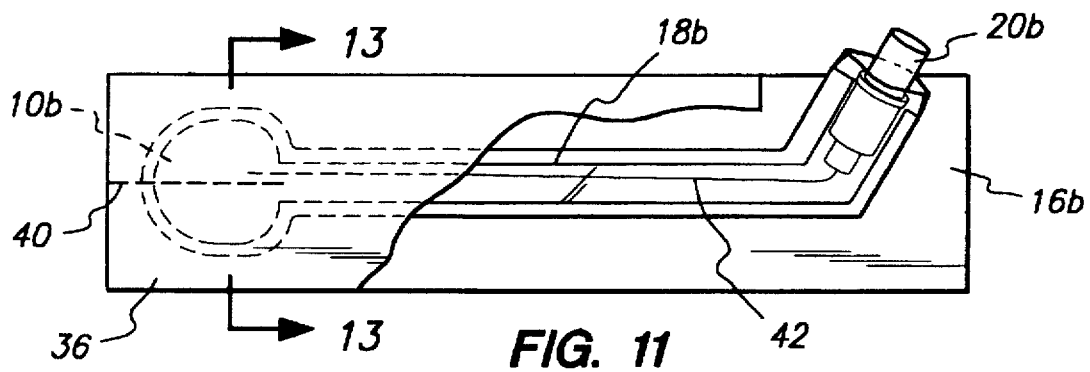
FIG. 11 is a plan view of a third embodiment of the anchor, employing a balloon having a securing patch disposed thereover wherein the patch is provided with an adhesive backing and a shielding strip is temporarily disposed over the backing.
Figure 12:
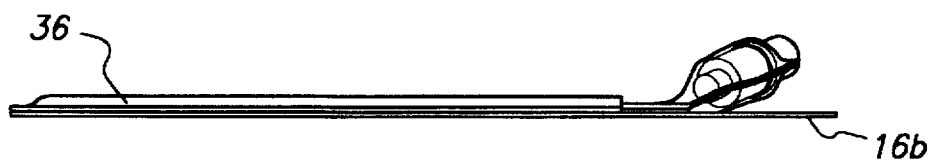
FIG. 12 is an elevational view of the anchor shown in FIG. 11.
Figure 13:
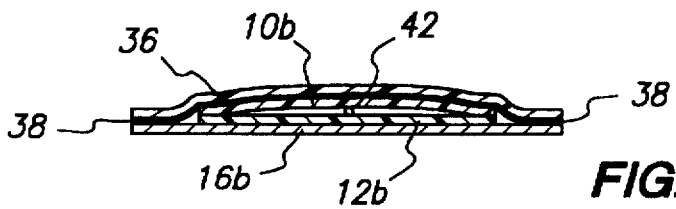
FIG. 13 is a cross-sectional view of the anchor shown in FIG. 11, taken on the plane designated by line 13—13.

The second embodiment balloon is applied and used in the same way as that of the first embodiment. As seen in FIG. 9, the balloon is adhered to the outside surface of a trocar sheath 22 so as to extend longitudinally of the sheath. The hourglass shape of the balloon 10a provides distal and proximal portions 30 and 32, respectively. Upon extension of the sheath 22 through the tissue as shown in FIG. 10, these portions are disposed to either side of the tissue 26 to anchor the sheath 22 against movement distally into or proximally out of the opening 28 through which the sheath extends. The necked-down portion of the balloon 10a, designated 34, does not significantly expand upon inflation of the portions 30 and 32. Constraint of the portion 34 is provided both by its reduced dimension, as compared to the portions 30 and 32, and its adherence to the second film layer 12a.

Like the first embodiment balloon, when in the deflated condition the balloon 10a assumes a low profile configuration essentially contiguous with the outside surface of the sheath 12. This minimizes trauma to the tissue both during insertion and removal of the sheath.

THIRD EMBODIMENT

As shown in FIGS. 11–15, the third embodiment is similar to that of the first embodiment, with the exception that the balloon, designated 10b, is a closed elastomeric envelope having top and bottom surfaces; and the backing strip is a patch 36 adhered to and extending over the balloon. The patch 36 is provided with contact adhesive 38 to either side of the balloon 10b. A removable paper or plastic shielding strip 16b extends across the balloon 10b and over the adhesive 38. Inflation tube 18b for the third embodiment is contiguous with the balloon 10b and also adhered beneath the patch 36. Contact adhesive 38 on the patch 36 is disposed to either side of the tube 18b and covered by the removable shielding strip 16b. A check valve or stop cock 20b is secured in the proximal end of the inflation tube 18b.

Figure 14:
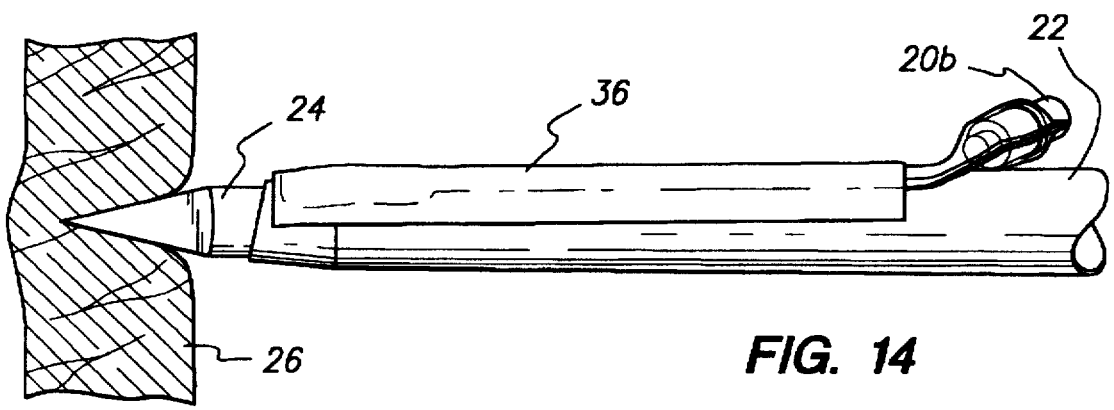
FIG. 14 is an elevational view of the FIG. 11 anchor in place on a trocar sheath, with the balloon of the anchor in a deflated condition and a trocar extended through the sheath in the process of forming a puncture opening in a tissue layer.
Figure 15:
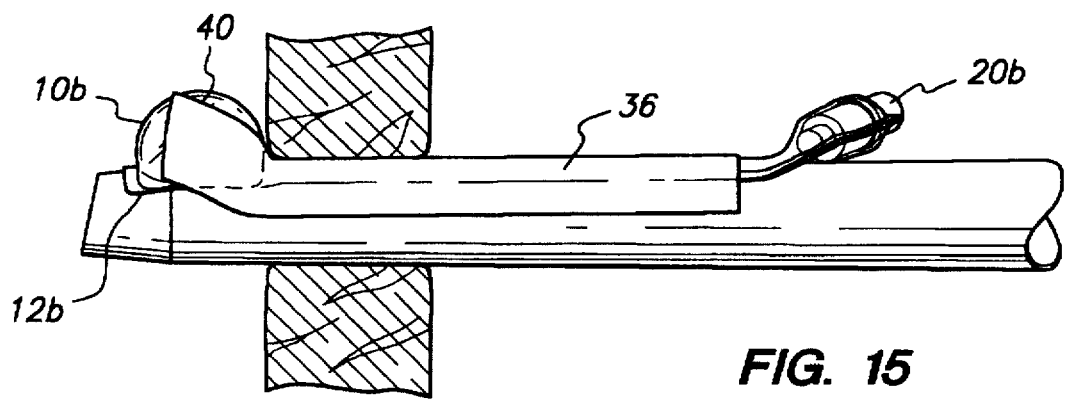
FIG. 15 is an elevational view similar to that of FIG. 14, showing the sheath fully extended through the puncture opening, with the balloon inflated and the trocar removed from the sheath.
Figure 16:
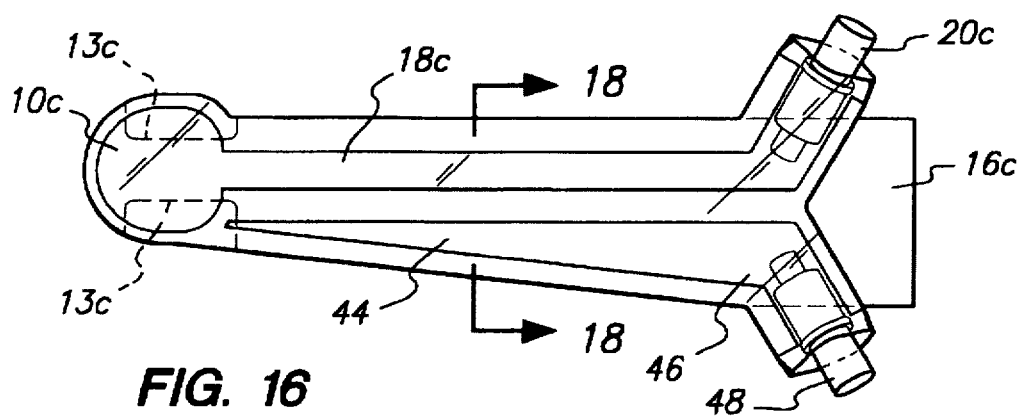
FIG. 16 is a plan view of a fourth embodiment of the anchor employing a balloon, wherein the balloon has two separately inflatable chambers and an adhesive backing with a shielding strip temporarily disposed over the backing.
Figure 17:
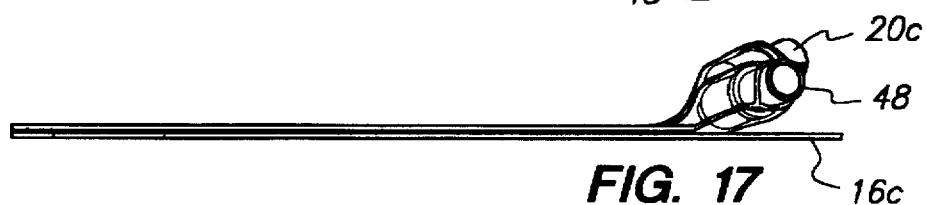
FIG. 17 is an elevational view of the anchor shown in FIG. 16.
Figure 18:
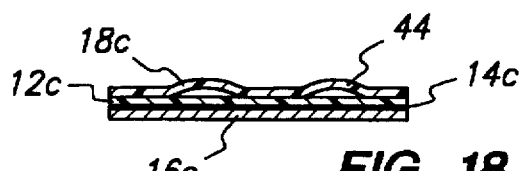
FIG. 18 is a cross-sectional view of the anchor shown in FIG. 16, taken on the plane designated by line 18—18.
Figure 19:
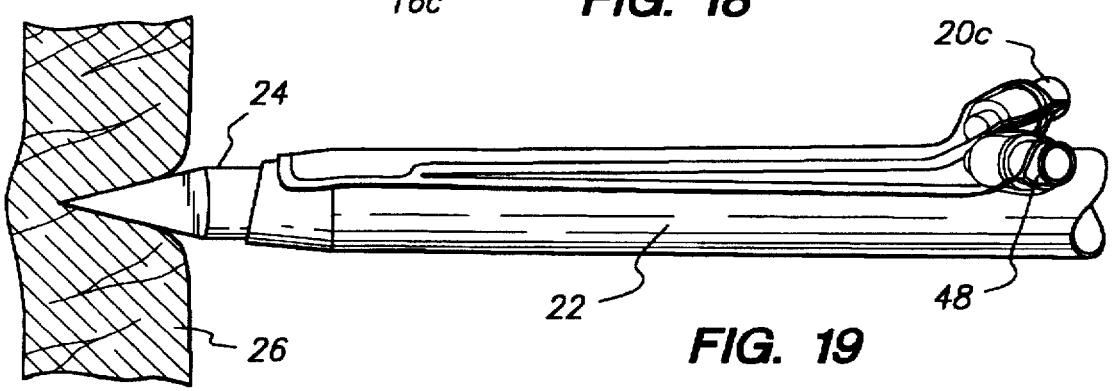
FIG. 19 is an elevational view of the FIG. 16 anchor in place on a trocar sheath with the balloon of the anchor in a deflated condition and the trocar extended through the sheath in the process of forming a puncture opening in a tissue layer.
Figure 20:
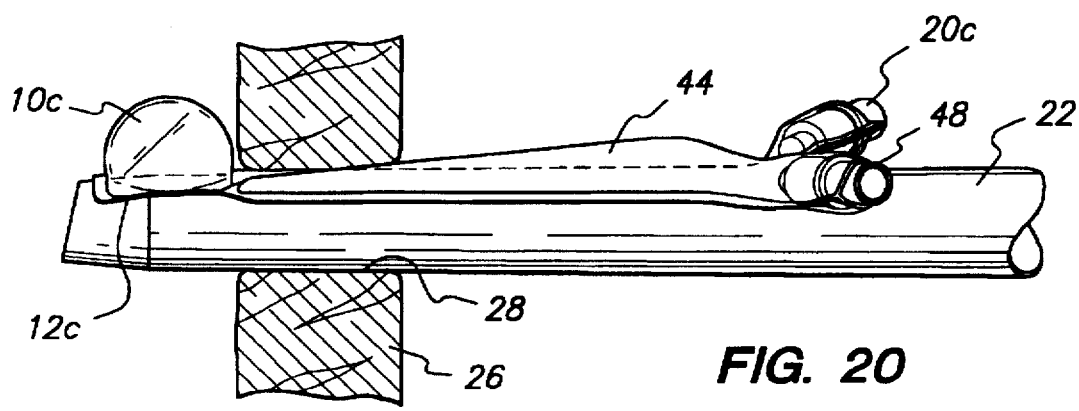
FIG. 20 is an elevational view similar to that of FIG. 19, showing the sheath fully extended through the puncture opening, with both chambers of the balloon inflated and the trocar removed from the sheath.

In use, the shielding strip 16b is removed from the adhesive 38 and the balloon assembly is secured directly to the outside surface of the instrument with which it is used by the patch 36. FIG. 14 shows the balloon so applied to a trocar sheath 22 having a trocar 24 extended therethrough. The adhesive 38 to either side of the balloon 10b and inflation tube 18b adheres directly to the smooth outside surface of the trocar sheath 22. A perforated tear line 40 is formed in the patch 36 over the balloon 10b.

Figure 40:
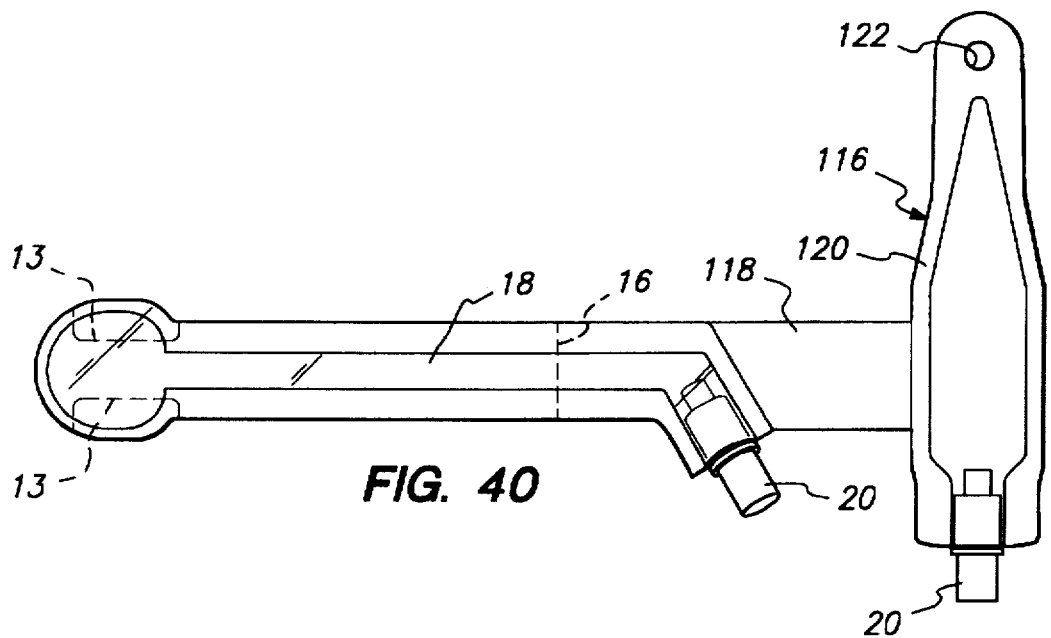
FIG. 40 is a plan view of a tenth embodiment of the anchor employing a distal balloon corresponding generally to that of the first embodiment and a proximal balloon connected to the distal balloon by a web.

Once secured in place as shown in FIG. 14, the third embodiment balloon 10b is extended through the tissue 26 in the same manner as the first embodiment balloon. After being extended fully through the tissue as shown in FIG. 40, the balloon is inflated to the inside of the tissue. Such inflation functions to tear the patch 36 along the frangible tear line 40. Upon completion of the surgical procedure or as otherwise desired, the balloon may be deflated to return to its condition closely contiguous to the sheath so that the sheath may be removed with a minimum of trauma.

The third embodiment sheath shown in FIGS. 11–15 is provided with a thin spacer string 42 between the inner and outer sides of the balloon 10b. Ideally, this string extends over the full length of the balloon 10b and inflation tube 18b so as to prevent the sides of the balloon and tube from fully closing against one another when the balloon is in the deflated condition. The space provided by the string provides a fluid passage and facilitates inflation of the balloon with a minimum of pressure. Although the string is only shown in the third embodiment, it should be understood that it might be applied to any of the embodiments discussed herein.

FOURTH EMBODIMENT

As shown in FIGS. 16–20, the fourth embodiment corresponds to the first embodiment, with the addition that it is provided with a second balloon 44 of an elongate-divergent configuration. The balloon 44, as may be seen in FIG. 16, diverges from the distal balloon, designated 10c. The balloons 10c and 44 provide separate inflation chambers. A separate inflation tube 46 having a check valve or stop cock 48 is provided for inflation of the balloon 44. The elements of the fourth embodiment corresponding to those of the first embodiment are designated by like numerals, followed by the letter c, as follows: balloon 10c; first film layer 12c; second film layer 12c; adhesive cut-away portions 13c; contact adhesive 14c; shielding strip 16c; inflation tube 18c; and, check valve or stop cock 20c.

The fourth embodiment anchor is applied to an instrument and surgically inserted in the same manner as the first embodiment anchor. Such an application may be seen in FIG. 19 wherein the fourth embodiment anchor is shown attached to the smooth outside surface of the trocar sheath 22 having a sharp tipped trocar 24 extended therethrough into piercing engagement with a layer of living tissue 26. Once extended through the tissue as shown in FIG. 20a, the balloon 10c is first inflated to the interior of the tissue to anchor the sheath against removal in the proximal direction. The second balloon 44 is then inflated to anchor the sheath against movement interiorally of the tissue in the distal direction relative to the user. The elongate tapered configuration of the balloon 44 accommodates tissue of virtually any thickness and can also serve to form a seal between the interior of the puncture 28 and the sheath 22. Upon completion of the surgical procedure, both balloons are deflated and the sheath is removed, with a minimum of trauma.

FIFTH EMBODIMENT

Figure 21:
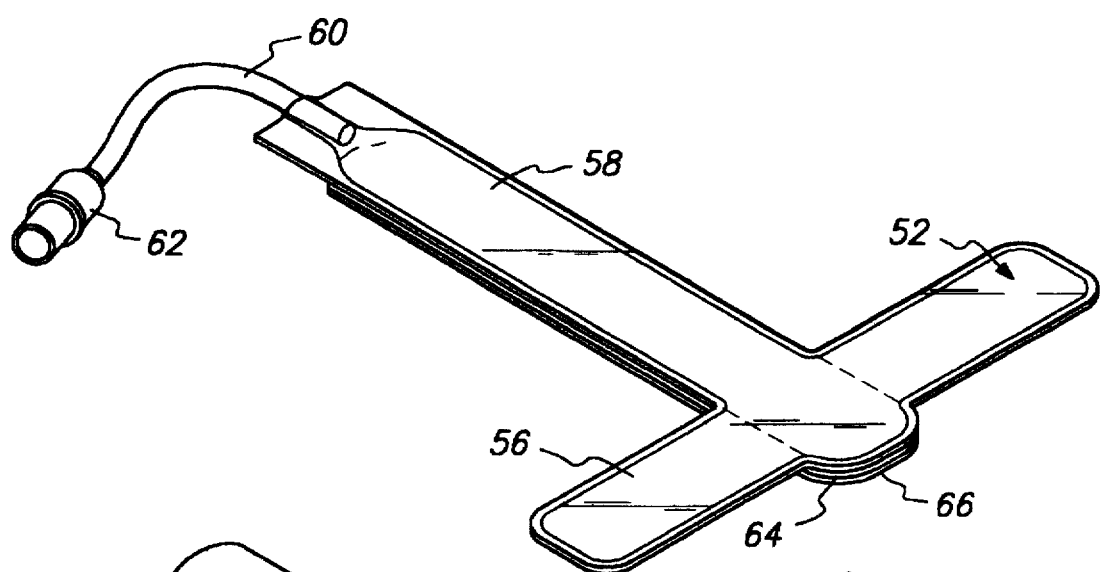
FIG. 21 is a perspective view of a fifth embodiment of the anchor employing a balloon with an adhesive backing, wherein the balloon is elongate and extends across the backing.
Figure 22:
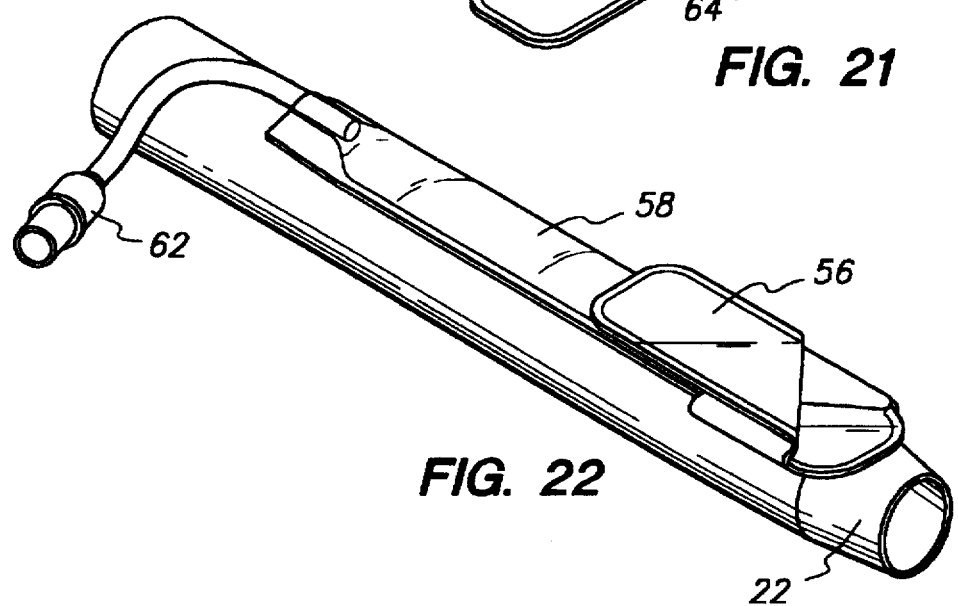
FIG. 22 is a perspective view of the anchor shown in FIG. 21 adhesively secured to a trocar sheath, with the balloon in a deflated condition folded against the sheath.
Figure 23:
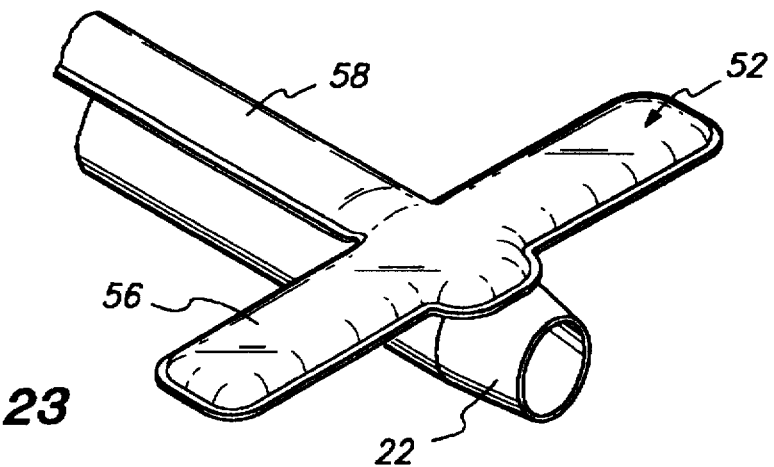
FIG. 23 is a perspective view similar to that of FIG. 22, showing the balloon inflated and extending transversely to either side of the sheath.

The balloon of this embodiment, as shown in FIGS. 21–23, is of a generally T-shaped configuration and fabricated of superimposed sheets of flexible inelastic film. The commercially available film known as Rexham 705517 has been found suitable.

FIG. 21 shows the fifth embodiment anchor in deflated condition as it would be supplied for use with any desired surgical instrument. The anchor comprises a balloon 52 fabricated of superimposed peripherally connected sheets of elastic, semi-elastic or inelastic flexible film. Preferably, semi-elastic urethane material is used. The balloon has an elongate transverse section 56 and a longitudinally extending section 58. An inflation tube 60 having a check valve or stop cock 62 is secured in fluid communication with the section 58. A contact adhesive layer is secured to and extends over the section 58. A removable shielding strip 66 is disposed over the adhesive 64. As shown, the adhesive 64 is adhered directly to the balloon 52.

The fifth embodiment anchor is adhered to the outside surface of an instrument and used in essentially the same manner as the first embodiment anchor. FIG. 22 shows the anchor secured to a trocar sheath 22. As there shown, the shielding strip 66 has been removed from the adhesive and the section 58 has been adhered longitudinally of the sheath with the adhesive 64. While FIG. 22 shows the ends of the transverse balloon section 56 folded over the section 58, it should be understood that these ends are not adhered to the sheath. The folded over condition is simply for purposes of reducing the profile of the balloon during insertion.

FIG. 23 shows the balloon as it would appear after inserted into place through a puncture and inflated. Such insertion would be carried out in essentially the same manner shown in FIGS. 4 and 5. Once in place with the transverse section 56 to the interior of the pierced tissue, inflation of the anchor functions to expand the transverse section transversely of the trocar sheath 22, thus securely anchoring the sheath against removal from the puncture opening. Upon completion of the surgical procedure, the balloon is deflated and may collapse against the sheath upon removal, with a minimum of trauma.

SIXTH EMBODIMENT

The sixth embodiment anchor is of an elongate toroidal configuration and adapted to be slipped over and around a surgical instrument, without need for an adhesive. As shown in FIGS. 24–27, this embodiment comprises: an elongate toroidal elastic balloon 68; spaced proximal and distal rings 70 and 72, respectively, disposed within the balloon 68; an intermediate ring 74 disposed around the balloon between the proximal and distal rings; and, an inflation tube 76 communicating with the interior of the balloon through a flange 78 on the ring 70. As shown, the balloon 68 is fabricated of a sleeve folded over upon itself with one end of the sleeve tied to the ring 72 by a cord 80 and the other end of the sleeve tied to the outside of the flange 78 by a cord 82.

Figure 24:
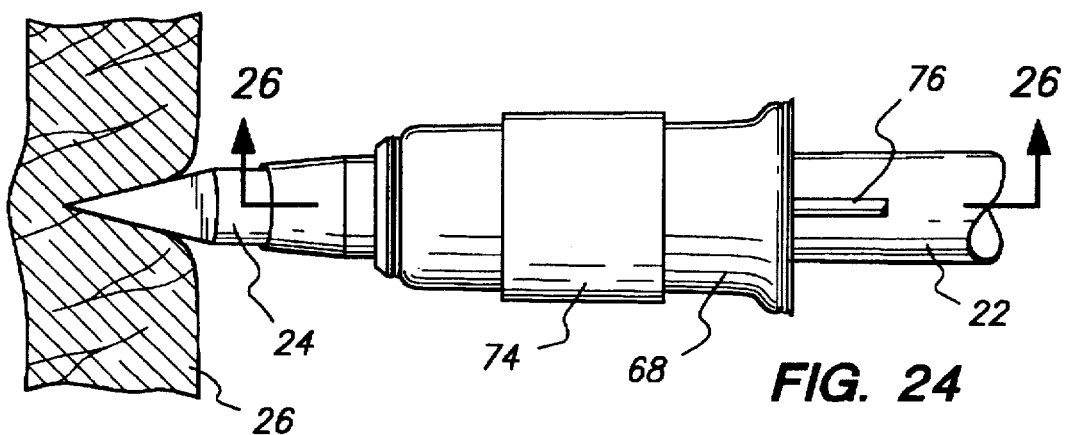
FIG. 24 is an elevational view of a sixth embodiment of the anchor in place on a trocar sheath, with the balloon of the anchor in a deflated condition and a trocar extended through the sheath in the process of forming a puncture opening in a tissue layer.
Figure 25:
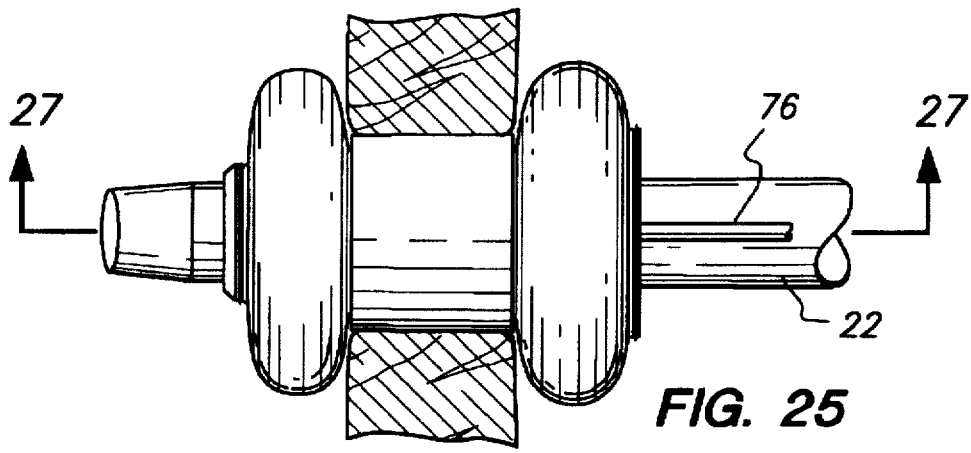
FIG. 25 is an elevational view similar to that of FIG. 24, showing the sheath fully extended through the puncture opening, with the balloon inflated and the trocar removed from the sheath.
Figure 26:
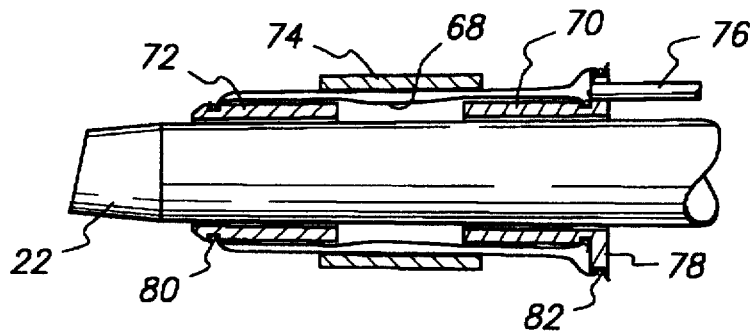
FIG. 26 is a cross-sectional view taken on the plane designated by line 26—26 of FIG. 24.
Figure 27:
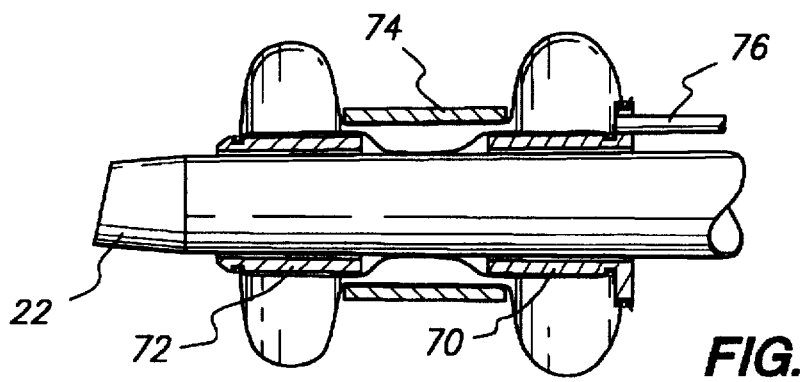
FIG. 27 is a cross-sectional view taken on the plane designated by line 27—27 of FIG. 25.

In use, the sixth embodiment anchor is simply slipped over the instrument to which it is applied. In the exemplary embodiment illustrated, the instrument comprises a trocar sheath 22. As shown in FIG. 24, the balloon is deflated and a sharp tipped trocar 24 extends through the sheath 22 into piercing engagement with a layer of living tissue 26. Once fully extended through the tissue, the balloon 68 is inflated as shown in FIG. 25 to expand to either side of the tissue. As so expanded, the balloon forms donut-shaped barriers to either side of the tissue. Expansion of the balloon within the thickness of the tissue is prevented by the ring 74. The space between the rings 72 and 70 permits the interior wall of the balloon to expand into gripping engagement with the sheath, as shown in FIG. 27. Thus, the sheath is anchored against movement into or out of the pierced tissue. Upon completion of the surgical procedure, the balloon is deflated and returns to the condition shown in FIG. 26, thus permitting removal of the anchor with a minimum of trauma.

To maintain the orientation of the rings in the sixth embodiment, one or more thin ribs may be provided between the proximal and distal rings 70 and 72. These ribs (not illustrated) are so proportioned and spaced so as not to interfere with inward expansion of the balloon into gripping engagement with the sheath, as shown in FIG. 27. The outer intermediate ring 74 may be adhered to the outside surface of the balloon 68 to prevent its displacement along the balloon.

SEVENTH EMBODIMENT

Figure 30:
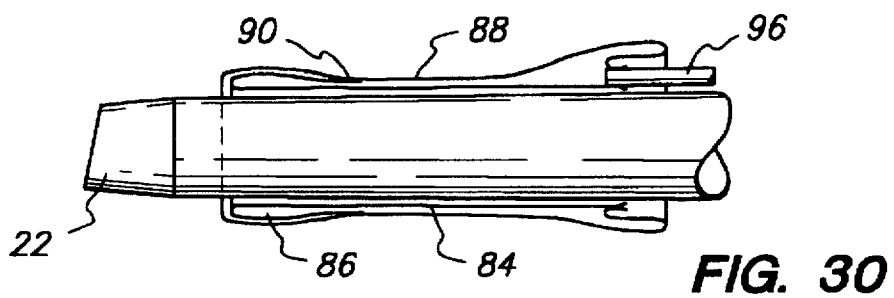
FIG. 30 is a cross-sectional view taken on the plane designated by line 30—30 of FIG. 28.
Figure 31:
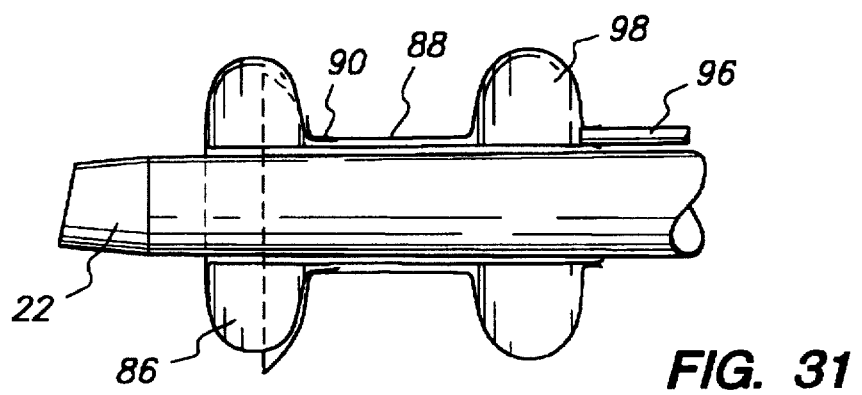
FIG. 31 is a cross-sectional view taken on the plane designated by line 31—31 of FIG. 29.

The seventh embodiment anchor is similar to that of the sixth embodiment in that it employs an elongate toroidal balloon adapted to be received around the instrument to be anchored. In the case of the seventh embodiment, however, the balloon is preferably fabricated so that the distal portion of the balloon is elastomeric and the proximal portion is inelastic. FIG. 30 shows such a construction wherein an inner elastomeric sleeve 84 is folded upon itself to provide a distal balloon section 86. An inelastic sleeve 88 is extended over the sleeve 84. The inelastic sleeve 84 is circumferentially welded to the folded over end of the inner sleeve 84 at a weld line 90. From the weld line to the distal end of the inelastic sleeve a perforated tear line 92 is provided to permit the sleeve to break upon expansion of the distal balloon section 86. The proximal end of the outer inelastic sleeve 88 is folded upon itself and circumferentially sealed to a flange member 94 by a tie. An inflation tube 96 extends through the flange member 94 into fluid communication with the interior of the balloon formed by the sleeves 84 and 88.

Figure 28:
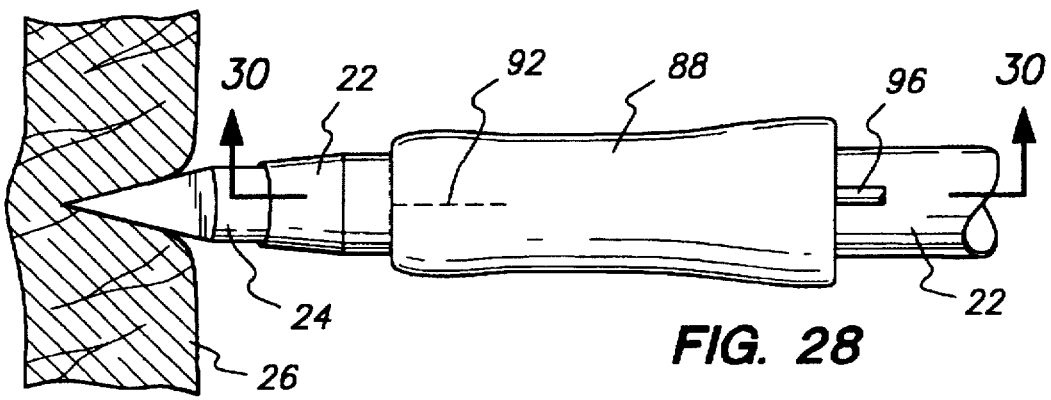
FIG. 28 is an elevational view of a seventh embodiment of the anchor in place on a trocar sheath, with the balloon of the anchor in a deflated condition and a trocar extended through the sheath in the process of forming a puncture opening in a tissue layer.
Figure 29:
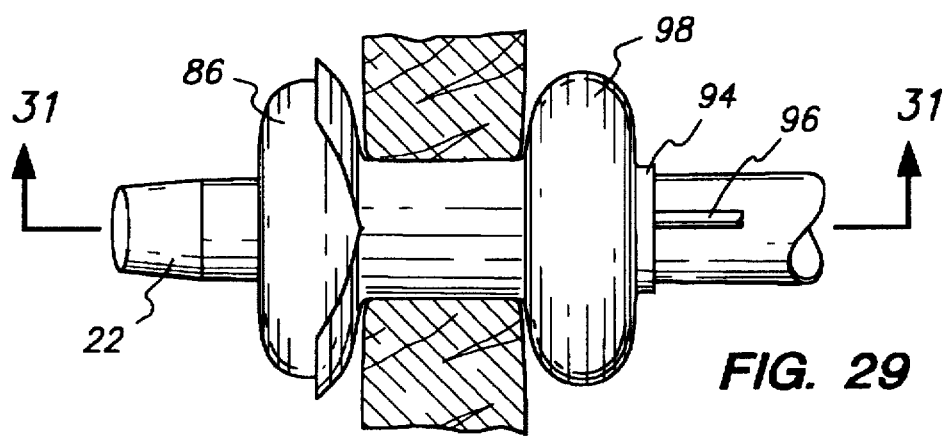
FIG. 29 is an elevational view similar to that of FIG. 28, showing the sheath fully extended through the puncture opening, with the balloon inflated and the trocar removed from the sheath.

In use, the seventh embodiment anchor is slipped around the instrument to be anchored. As shown in FIG. 28, the instrument comprises a trocar sheath 22 having a sharp tipped trocar 24 extending therethrough in the process of piercing an opening in a layer of living tissue 26. The trocar is pushed fully through the tissue, together with the anchor. Once in place, as shown in FIG. 29, the trocar is removed and the balloon is inflated. Inflation functions to form toroidal balloon sections to either side of the tissue and to interiorally expand the balloon into gripping engagement with the sheath. Thus, the sheath is anchored against movement into or out of the tissue.

It will be appreciated that upon expansion of the distal balloon section 86 the inelastic sleeve tears along the tear line 92. That portion of the sleeve 88 within the tissue remains intact and functions to constrain the balloon. The proximal end of the balloon, designated 98, expands to a toroidal configuration by unfolding the folded over portions of the sleeve 88 (see FIG. 30). Upon completion of the surgical procedure, the balloon is deflated, thus permitting the anchor to be removed with a minimum of trauma.

EIGHTH EMBODIMENT

Figure 32:
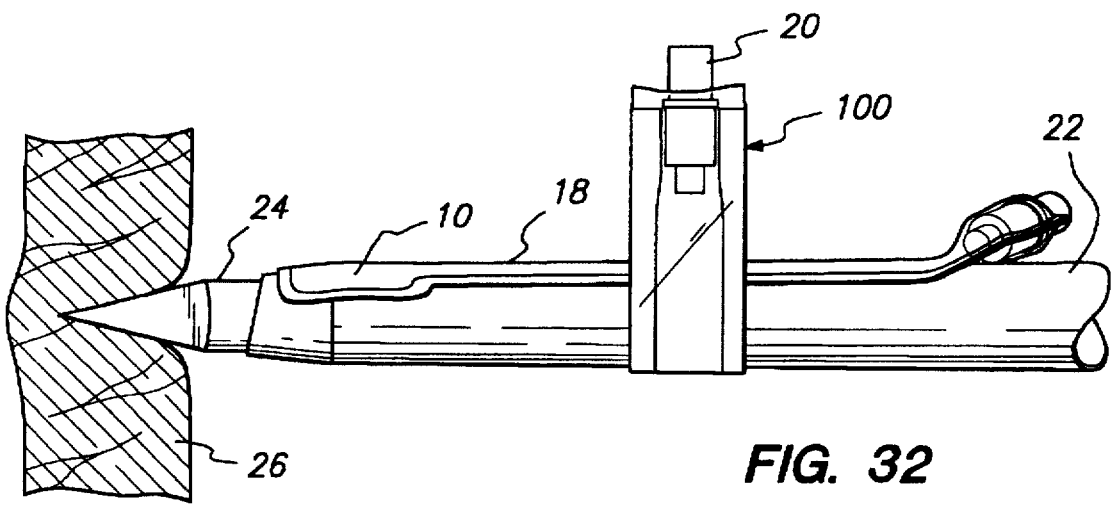
FIG. 32 is an elevational view of an eighth embodiment of the anchor in place on a trocar sheath with the balloon of the anchor in a deflated condition and a trocar extended through the sheath in the process of forming a puncture opening in a tissue layer.
Figure 33:
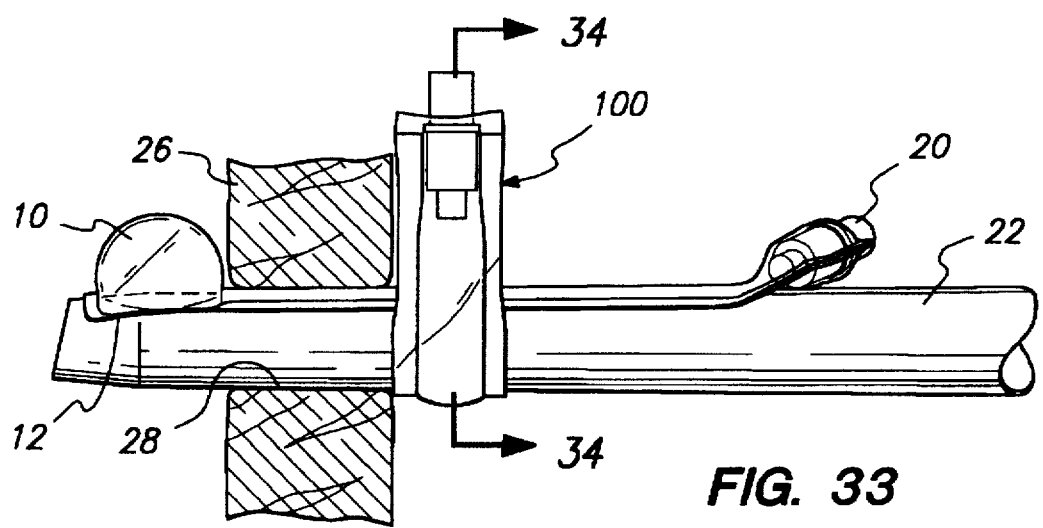
FIG. 33 is an elevational view similar to that of FIG. 32, showing the sheath fully extended through the puncture opening, with the balloons of the anchor inflated and the trocar removed from the sheath.
Figure 34:
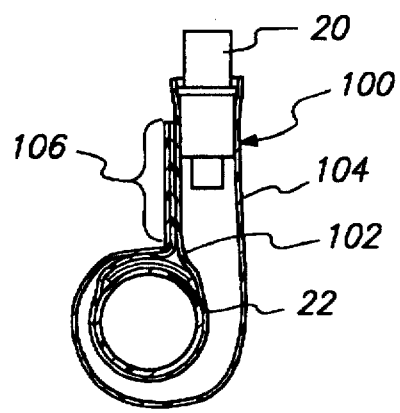
FIG. 34 is a cross-sectional view taken on the plane designated by line 34—34 of FIG. 33.
Figure 35:
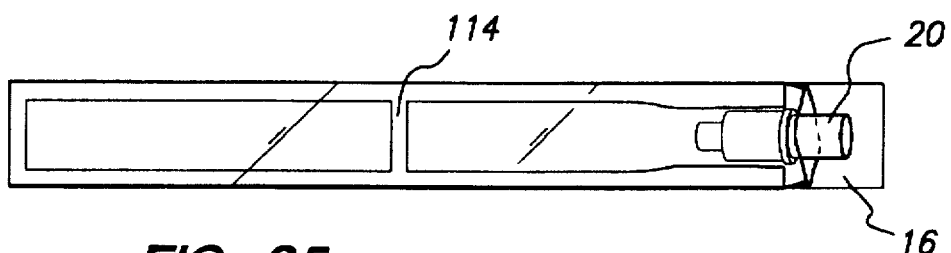
FIG. 35 is a plan view of a flat balloon adapted to be wrapped around a trocar sheath to provide a generally angular balloon in a ninth embodiment of the anchor.

This embodiment is illustrated in FIGS. 32–34 and corresponds to the first embodiment, with the addition that it is provided with a toroidal balloon assembly 100 adapted to be slidably received around the balloon 10 and its air passage 18. Elements of the eighth embodiment corresponding to those of the first embodiment are designated by like numerals. The purpose of the toroidal balloon assembly 100 is to provide an anchor "ring" which can be freely moved along a trocar sheath or other instrument to which the balloon 10 is adhered to provide a skin-side anchor which may be adjusted to accommodate the thickness of the tissue (e.g., abdominal wall) through which the sheath is extended. Initially, the balloon assembly is in a deflated condition and freely movable along the sheath. Upon being adjusted to the desired position (see FIG. 33), the assembly is inflated, thus causing its inner diameter to decrease into secure gripping engagement with the sheath.

Ideally, the balloon assembly 100 is fabricated with an elastic or semi-elastic inner film layer 102 and an elastic or semi-elastic outer film layer 104 which are peripherally RF welded together. The materials for these layers may be the same as those suggested for the balloon of the first embodiment. A check valve or stop cock 20 is sealingly secured in the open end of the balloon assembly 100.

The inner construction of the toroidal balloon assembly 100 is illustrated in FIG. 34. As there seen, the assembly is elongate and wrapped upon itself to form a toroidal configuration. The proximal and distal ends of the elongate balloon are adhered or welded together at area 106. The trocar sheath 22 is shown slidably received within the toroid provided by the assembly.

In use of the eighth embodiment, the balloon 10 would be secured to the sheath in a manner identical to that described with respect to the first embodiment. The toroidal balloon assembly 100 would then be slid over the sheath in a deflated condition. Then the sheath would be passed through the tissue 26 and anchored against removal by inflation of the balloon 10, as shown in FIG. 29. The deflated toroidal assembly 100 would then be adjusted along the length of the sheath to engage the outside of the tissue and then inflated, as shown in FIG. 33. The latter inflation functions to expand the assembly 100 into gripping engagement with the sheath and anchor the sheath against movement distally relative to the tissue.

NINTH EMBODIMENT

This embodiment is shown in FIGS. 35–39 and is similar to the eighth embodiment in that it is used with the distal balloon 10 of the first embodiment and provides a skin-side anchor. It differs from the eighth embodiment only in the construction of the skin-side anchor assembly, designated 108. Elements of the ninth embodiment corresponding to those of the first embodiment are designated by like numerals.

The anchor assembly 108 is similar to the assembly 100 in that it is fabricated of an elastic or semi-elastic inner film layer 110 and an inelastic or semi-elastic outer film layer 112 peripherally RF welded together to provide a balloon. In the case of the assembly 108, however, a weld line 114 is formed to extend across the assembly intermediate its length so that the balloon only extends over approximately one-half of the length of the assembly (see FIG. 35). Also, in the case of the ninth embodiment, the distal and proximal ends of the assembly are not welded together, but rather are provided with contact adhesive 14 whereby they may be selectively secured together after being wrapped around an instrument. A check valve or stock cock 20 is sealingly received in the open end of the balloon provided by the assembly 108.

Figure 38:
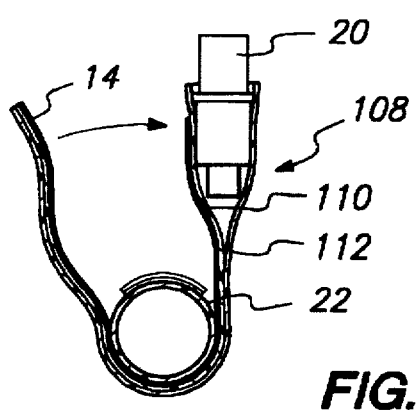
FIG. 38 is a cross-sectional view taken on the plane designated by line 38—38 of the FIG. 36.
Figure 39:
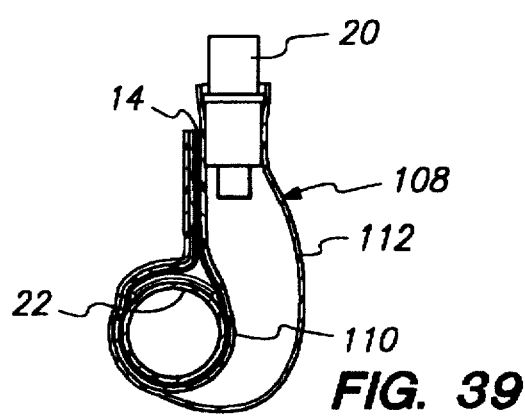
FIG. 39 is a cross-sectional view taken on the plane designated by line 39—39 of FIG. 37.

FIGS. 38 and 39 show how the assembly 108 is placed around the trocar sheath 22. In FIG. 38, the assembly is being wrapped around the sheath. In FIG. 39, the distal and proximal ends of the assembly have been secured together by the adhesive 14 and the balloon has been inflated to expand the assembly into gripping engagement with the sheath.

Figure 37:
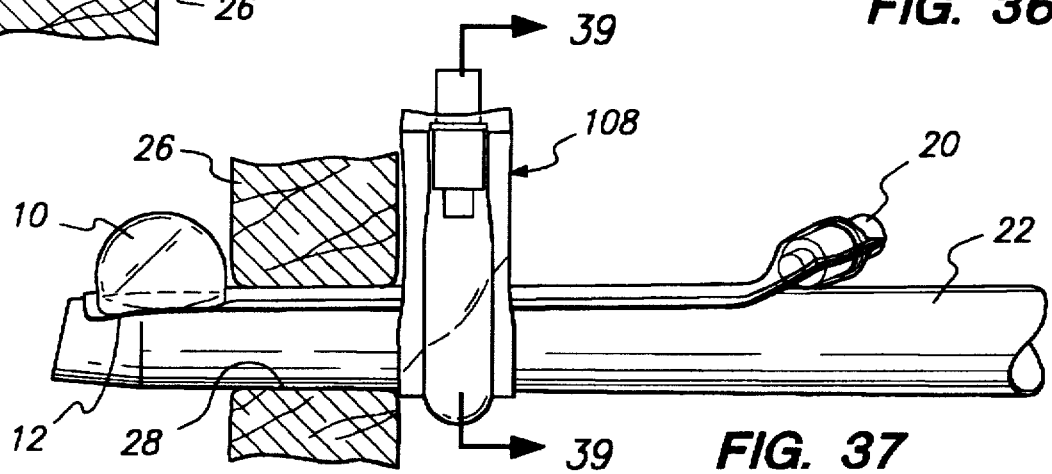
FIG. 37 is an elevational view similar to that of FIG. 36, showing the sheath fully extended through the puncture opening, with the balloons inflated and the trocar removed from the sheath.

In use, the ninth embodiment anchor is passed through a tissue layer in the same manner as the first embodiment anchor and the distal balloon 10 is then inflated, as seen in FIG. 37. Then the assembly 108 is slid along the sheath 22 into engagement with the outside surface of the tissue. Once so engaged, the assembly is inflated to securely engage the assembly with the outside surface of the sheath and anchor the sheath against distal movement relative to the tissue.

Figure 36:
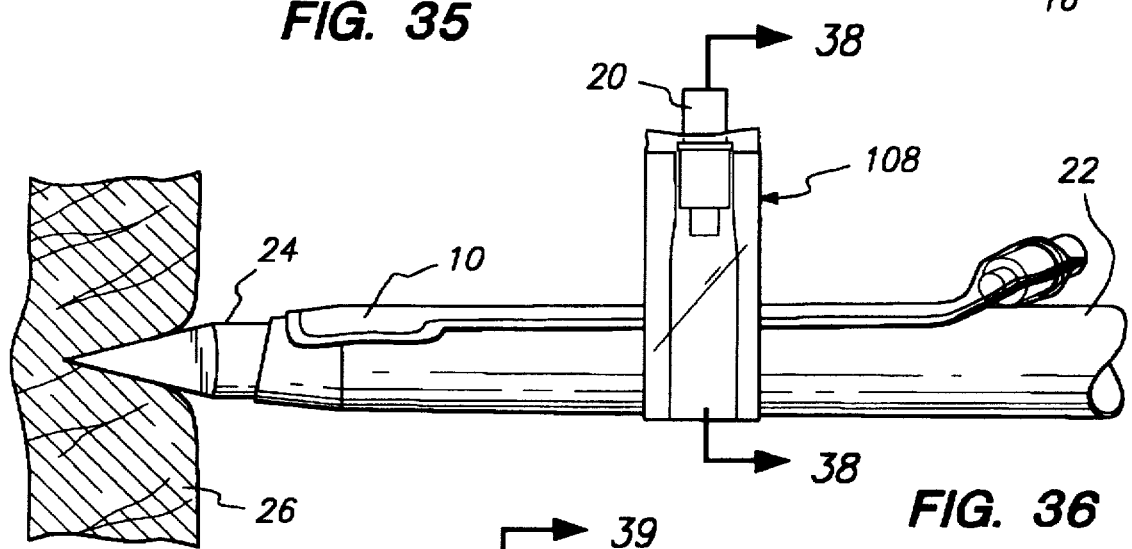
FIG. 36 is an elevational view of the ninth embodiment of the anchor in place on a trocar sheath, with the balloons of the anchor in a deflated condition and a trocar extending through the sheath in the process of forming a puncture opening in a tissue layer.

FIG. 36 shows the assembly 108 in place around the sheath prior to extension of the sheath through the tissue layer 26. As an alternative, the assembly could be wrapped around the sheath after it has been extended through the tissue. Such a procedure is possible because the assembly is capable of being wrapped around the sheath after it is in place within a layer of body tissue.

TENTH EMBODIMENT

This embodiment is shown in FIGS. 40–44 and also incorporates the distal balloon of the first embodiment. In the case of the tenth embodiment, however, a skin-side anchor assembly 116 is connected in transverse relationship to the inflation tube 18 by a flexible web 118. Elements of the tenth embodiment corresponding to those of the first embodiment are designated by like numerals.

The assembly 116 and web 118 are fabricated from continuations of the film layers forming the balloon 10 and the tube 18. These layers are peripherally welded together at a weld line 120 extending around the assembly 116. One end of the assembly 116 is open and sealingly receives a check valve or stock cock 20. An aperture 122 proportioned for receipt over the distal end of the valve 20 is formed in the end of the assembly 116 opposite that which receives the valve.

Figure 41:
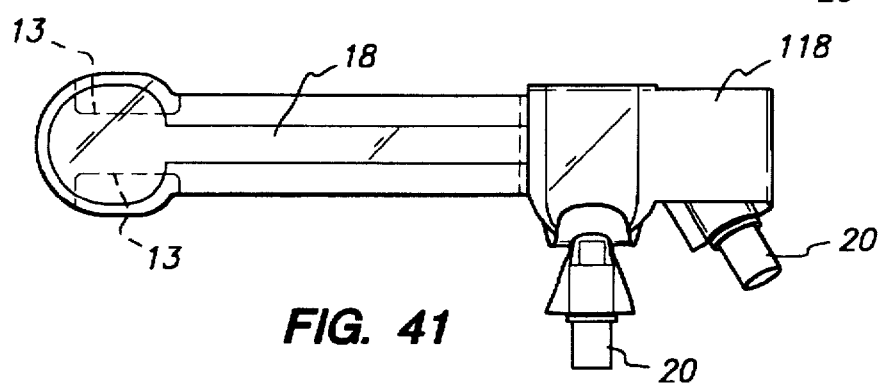
FIG. 41 is a plan view of the tenth embodiment anchor wherein the proximal balloon has been folded over and wrapped around the air passage leading to the distal balloon.

To prepare the tenth embodiment for use, the web 118 is folded over the tube 18 to dispose the first elastic film layer 11 of the assembly in opposition to the tube 18. Then the assembly is wrapped around the inflation tube 118 to engage the aperture 122 over the distal end of the valve 20, as shown in FIG. 41. With the assembly 116 so prepared, the generally toroidal balloon provided by the anchor may be slipped over an instrument, such as a trocar sheath, with which it is used. Initially, the shielding strip 16 would be left in place as the anchor is so positioned. Once the balloon 10 is positioned as desired, its distal end would be lifted and the shielding strip would be removed. Then the balloon 10 and the inflation tube 18 would be pressed into secure adhered relationship with the outside of the instrument, as shown in FIG. 42.

Figure 42:
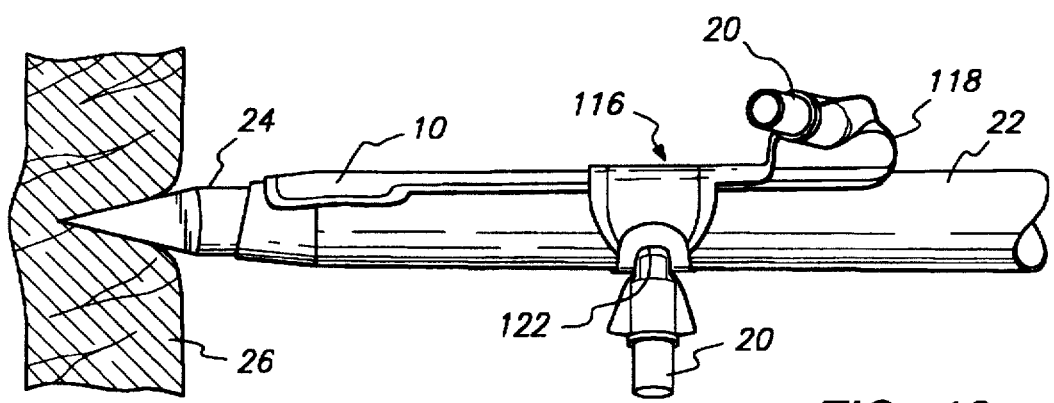
FIG. 42 is an elevational view of the tenth embodiment anchor in place on a trocar sheath, with the balloons of the anchor in a deflated condition and a trocar extending through the sheath in the process of forming a puncture opening in a tissue layer.
Figure 43:
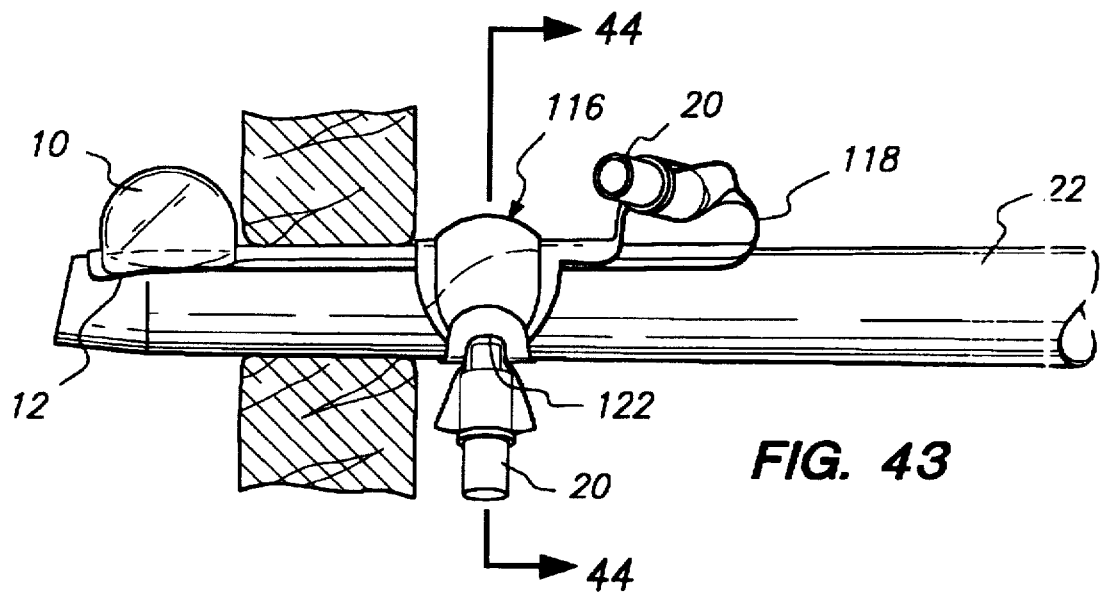
FIG. 43 is an elevational view similar to that of FIG. 42, showing the sheath fully extended through the puncture opening, with the balloons inflated and the trocar removed from the sheath; and, FIG. 44 is a cross-sectional view taken on the plane designated by line 44—44 of FIG. 43.
Figure 44:
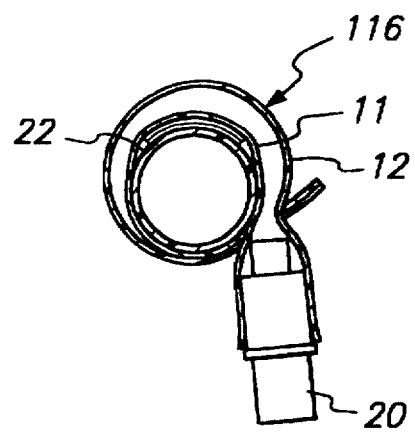

With the tenth embodiment anchor in place on a trocar sheath as shown in FIG. 42 and the balloons in deflated condition, the sheath is initially passed through a tissue layer and anchored with the distal balloon 10 in same manner as the first embodiment. Once so in place, the assembly 116 is slid along the sheath into engagement with the outside of the tissue, as shown in FIG. 43, and inflated. The flexibility of the web 118 facilitates such adjustment. Inflation of the assembly 116 serves to secure the assembly against movement relative to the sheath and anchor the sheath against distal movement.

Conclusion

From the foregoing description, it is believed apparent that the present invention enables the attainment of the objects initially set forth herein. In particular, it provides an anchor which may be readily applied to any surgical instrument without modification of the instrument and which may be used with a minimum of trauma to the patient. While all embodiments serve as effective anchors, the tenth embodiment is considered the preferred embodiment because of its ease of manufacture from two layers of film material and the secure anchor which it provides against both proximal and distal movement. It should be understood, however, that the invention is not intended to be limited to the specifics of the illustrated embodiments, but rather is defined by the accompanying claims.

What is claimed as the invention is:

1. A method of anchoring an instrument having a generally smooth outer surface in a puncture opening extending through a body tissue having an interior, an inside and an outside, and a thickness, said method comprising:
    a) securing a balloon to the outer surface of the instrument so that the balloon has a low profile essentially contiguous with said surface when the balloon is in a contracted non-inflated condition and an expanded high profile condition when the balloon is inflated;
    b) connecting a conduit in fluid communication with the balloon and securing the conduit to the outer surface of the instrument by a contact adhesive on the conduit;
    c) extending the instrument through the puncture opening from the outside to the inside to dispose at least a portion of the balloon to the inside of the tissue while the conduit extends to the outside of the body tissue; and,
    d) inflating the balloon through the conduit to engage the tissue and anchor the instrument within the opening.

2. A method of anchoring an instrument having a generally smooth outer surface in a puncture opening extending through a body tissue having an interior, an inside and an outside, and a thickness, said method comprising:
    a) extending an elongate balloon across the instrument to provide unrestrained free ends of the balloon disposed laterally of the instrument and an intermediate portion of the balloon secured to one side only of the instrument so that the balloon has a low profile essentially contiguous with said surface when the balloon is in a contracted non-inflated condition and an expanded high profile condition when the balloon is inflated;
    b) extending the instrument through the puncture opening from the outside to the inside to dispose at least a portion of the balloon to the inside of the tissue; and,
    c) inflating the balloon to engage the tissue and anchor the instrument within the opening.

3. A method of anchoring an instrument having a generally smooth outer surface in a puncture opening extending through a body tissue having an interior, an inside and an outside, and a thickness, said method comprising:
    a) securing an elongate balloon having proximal and distal ends and a length exceeding the thickness of the body tissue to the outside surface of the instrument to dispose the balloon in a condition extending longitudinally of the instrument so that the balloon has a low profile essentially contiguous with said surface when the balloon is in a contracted non-inflated condition and an expanded high profile condition when the balloon is inflated;
    b) extending the instrument through the puncture opening from the outside to the inside to dispose the proximal and distal ends of the balloon to either side of the body tissue; and,
    c) inflating the balloon so that the proximal and distal ends of the balloon expand to an enlarged profile to either side of the tissue to engage the tissue and anchor the instrument within the opening.

4. A method according to claim 3, wherein the balloon is of an elongated hourglass-shaped configuration.

5. A method of anchoring an instrument having a generally smooth outer surface in a puncture opening extending through a body tissue having an interior, an inside and an outside, and a thickness, said method comprising:
    a) securing a balloon comprised of superimposed sheets to the outer surface of the instrument so that the balloon has a low profile essentially contiguous with said surface when the balloon is in a contracted non-inflated condition and an expanded high profile condition when the balloon is inflated;

b) providing a thin spacer between the superimposed sheets to provide a fluid passage between the sheets when the balloon is in contracted non-inflated condition;

c) extending the instrument through the puncture opening from the outside to the inside to dispose at least a portion of the balloon to the inside of the tissue; and, d) inflating the balloon to engage the tissue and anchor the instrument within the opening.

6. A method of anchoring an instrument having a generally smooth outer surface in a puncture opening extending through a body tissue having an interior, an inside and an outside, and a thickness, said method comprising:

a) securing an elongate balloon having individually inflatable first and second chambers to the outside surface of the instrument to dispose the first chamber at one end of the balloon and the second chamber in a condition extending lengthwise of the instrument so that the balloon has a low profile essentially contiguous with said surface when the balloon is in a contracted non-inflated condition and an expanded high profile condition when the balloon is inflated;

b) extending the instrument through the puncture opening from the outside to the inside to dispose the first chamber to the inside of the tissue and the second chamber within the interior of the puncture; and, c) inflating the balloon to engage the tissue and anchor the instrument within the opening.

7. A method according to claim 6 wherein the second chamber has a wedge-shaped configuration diverging outwardly longitudinally of the instrument from the vicinity of the first chamber.

8. A method of anchoring an instrument having a generally smooth outer surface in a puncture opening extending through a body tissue having an interior, an inside and an outside, and a thickness, said method comprising:

a) extending a balloon of a toroidal configuration around the instrument so that the balloon has a low profile essentially contiguous with said surface when the balloon is in a contracted non-inflated condition and an expanded high profile condition when the balloon is inflated;

b) extending the instrument through the puncture opening from the outside to the inside to dispose at least a portion of the balloon to the inside of the tissue; and, c) inflating the balloon to extend a portion of the balloon into compression imparting relationship to the instrument and secure the balloon to the outer surface of the instrument and expand the balloon into engagement with the tissue and anchor the instrument within the opening.

9. A method of anchoring an instrument having a generally smooth outer surface in a puncture opening extending through a body tissue having an interior, an inside and an outside, and a thickness, said method comprising:

a) extending an elongate balloon lengthwise of the instrument and securing the balloon to the instrument so that the balloon has a low profile essentially contiguous with said surface when the balloon is in a contracted non-inflated condition and an expanded high profile condition when the balloon is inflated;

b) extending the instrument through the puncture opening from the outside to the inside to dispose portions of the balloon to either side of the body tissue; and, c) constraining an intermediate portion of the balloon against expansion while inflating the balloon to expand the portions to either side of the body tissue into engagement with the tissue and anchor the instrument within the opening.

10. A method of anchoring an instrument having a generally smooth outer surface in a puncture opening extending through a body tissue having an interior, an inside and an outside, and a thickness, said method comprising:

a) securing a balloon to the outer surface of the instrument by a patch disposed over the balloon and having portions to either side of the balloon adhered in engagement with the instrument so that the balloon has a low profile essentially contiguous with said surface when the balloon is in a contracted non-inflated condition and an expanded high profile condition when the balloon is inflated;

b) extending the instrument through the puncture opening from the outside to the inside to dispose at least a portion of the balloon to the inside of the tissue; and, c) inflating the balloon to engage the tissue and anchor the instrument within the opening.

11. A method according to claim 10, wherein said patch has a tear-away portion disposed over a portion of the balloon, said tear-away portion being frangible upon inflation of the balloon.

12. A method of anchoring an instrument having a generally smooth outer surface in a puncture opening extending through a body tissue having an interior, an inside and an outside, and a thickness, said method comprising:

a) securing a balloon to the outer surface of the instrument so that the balloon has a low profile essentially contiguous with said surface when the balloon is in a contracted non-inflated condition and an expanded high profile condition when the balloon is inflated;

b) extending the instrument through the puncture opening from the outside to the inside to dispose at least a portion of the balloon to the inside of the tissue;

c) inflating the balloon to engage the tissue and anchor the instrument within the opening; and, d) extending a secondary anchor around the instrument for longitudinal movement relative thereto towards and away from the balloon, said secondary anchor having an expansible chamber which maybe inflated to selectively engage the instrument and secure the secondary anchor against longitudinal movement relative thereto.

13. A method according to claim 6 wherein the secondary anchor comprises a toroidal balloon having an inside formed from an elastomeric film material and an outside formed from a flexible generally inelastic film material.

14. A method according to claim 6, wherein the secondary anchor comprises an elongate flexible member wrapped around the instrument and secured in a generally toroidal configuration.

15. A method according to claim 6 further comprising securing the balloon and secondary anchor by a flexible connecting element of sufficient length to enable the secondary anchor to move longitudinally relative to the balloon.

16. A method according to claim 6 wherein the balloon and secondary anchor are formed from common first and second flexible films peripherally joined to provide the balloon and the expansible chamber.

17. A method according to claim 16 wherein the first flexible film is elastomeric and disposed to face inwardly in opposition to the instrument and the second film is generally inelastic and disposed outside of the first film relative to the instrument with which the balloon is engaged.

* * * * *

UNITED STATES PATENT AND TRADEMARK OFFICE
CERTIFICATE OF CORRECTION

PATENT NO. : 5,697,946
DATED : December 16, 1997
INVENTOR(S) : Phillip K. Hopper et al.

It is certified that error appears in the above-identified patent and that said Letters Patent is hereby corrected as shown below:

```
              On the title page;
  item [75],   please add --Charles Gresl, San Francisco, CA--.
```

In column 14, line 44, please change "6" to --12--.

In column 14, line 48, please change "6" to --12--.

In column 14, line 52, please change "6" to --12--.

In column 14, line 56, please change "6" to --12--.

Signed and Sealed this

Seventeenth Day of November, 1998

Attest:

BRUCE LEHMAN

*Attesting Officer*    *Commissioner of Patents and Trademarks*